(12) United States Patent
Beer et al.

(10) Patent No.: US 8,852,325 B2
(45) Date of Patent: Oct. 7, 2014

(54) DEVICE FOR COLLECTING PARTICLES THAT HAVE A STRONG ELECTRON AFFINITY

(75) Inventors: Sebastian Beer, München (DE); Gerhard Müller, Grafing (DE); Jan Spannhake, Ottobrunn (DE); Wolfgang Legner, Höhenkirchen-Siegertsbrunn (DE)

(73) Assignee: EADS Deutschland GmbH, Ottobrunn (DE)

( * ) Notice: Subject to any disclaimer, the term of this patent is extended or adjusted under 35 U.S.C. 154(b) by 607 days.

(21) Appl. No.: 13/129,252

(22) PCT Filed: Nov. 24, 2009

(86) PCT No.: PCT/EP2009/065740
§ 371 (c)(1),
(2), (4) Date: Jul. 19, 2011

(87) PCT Pub. No.: WO2010/060905
PCT Pub. Date: Jun. 3, 2010

(65) Prior Publication Data
US 2011/0265653 A1    Nov. 3, 2011

(30) Foreign Application Priority Data
Nov. 26, 2008    (DE) .......................... 10 2008 059 113

(51) Int. Cl.
| | | |
|---|---|---|
| B03C 3/10 | (2006.01) | |
| B03C 3/74 | (2006.01) | |
| B03C 3/78 | (2006.01) | |
| B03C 3/16 | (2006.01) | |
| B03C 3/00 | (2006.01) | |
| G01N 33/00 | (2006.01) | |
| G01N 27/62 | (2006.01) | |
| G01N 1/40 | (2006.01) | |

(52) U.S. Cl.
CPC .......... *G01N 33/0057* (2013.01); *G01N 27/622* (2013.01); *G01N 2001/4038* (2013.01)
USPC ................ 96/50; 96/40; 96/41; 96/42; 96/43; 96/44; 96/45; 96/46; 96/47; 96/48; 96/49; 95/71; 95/72; 95/73; 95/74; 95/75

(58) Field of Classification Search
CPC .............. B03C 3/12; B03C 3/38; B03C 3/49; B03C 3/74; B03C 3/78; B03C 3/155
USPC ....................... 95/71–75; 96/40–50
See application file for complete search history.

(56) References Cited

U.S. PATENT DOCUMENTS 3,357,159 A * 12/1967 Drenning .......................... 96/32
3,704,572 A    12/1972 Gourdine et al.
(Continued)

FOREIGN PATENT DOCUMENTS

| DE | 10 2007 029549 | 1/2009 |
| EP | 1059521 | 12/2000 |
| WO | WO 2008/111403 | 9/2008 |

*Primary Examiner* — Amber Orlando
(74) *Attorney, Agent, or Firm* — Hoffmann & Baron, LLP

(57) ABSTRACT

A device for collecting particles that have a high electron affinity, particularly explosive particles, from a gas, includes a flow channel (12a) in which at least one electrically positive collector electrode (20a) and at least one ionising electrode (18a) are arranged, between which an electrical field is present so that the particles having high electron affinity can be indirectly charged by corona discharge on the ionising electrode (18a) and can be displaced towards the collector electrode (20a).

8 Claims, 5 Drawing Sheets

(56) References Cited

U.S. PATENT DOCUMENTS

| | | | |
|---|---|---|---|
| 4,066,526 A | * | 1/1978 | Yeh .................. 204/554 |
| 4,713,092 A | | 12/1987 | Kikuchi et al. |
| 4,898,105 A | * | 2/1990 | Rappoldt et al. ............ 110/245 |
| 5,012,159 A | * | 4/1991 | Torok et al. .............. 315/111.91 |
| 5,892,141 A | | 4/1999 | Jones et al. |
| 6,004,376 A | | 12/1999 | Frank |
| 6,152,988 A | * | 11/2000 | Plaks et al. ................ 95/58 |
| 6,436,170 B1 | | 8/2002 | McDermott et al. |
| 6,822,225 B2 | * | 11/2004 | Xu et al. ................ 250/287 |
| 7,453,060 B2 | | 11/2008 | Miller et al. |
| 2002/0141131 A1 | * | 10/2002 | Gorczyca et al. ............ 361/231 |
| 2003/0045192 A1 | * | 3/2003 | Midkiff et al. ............... 442/103 |
| 2004/0164238 A1 | * | 8/2004 | Xu et al. ................ 250/287 |
| 2006/0150816 A1 | * | 7/2006 | Jaisinghani ................ 96/67 |
| 2006/0278082 A1 | * | 12/2006 | Tomimatsu et al. ............ 96/66 |
| 2007/0261556 A1 | * | 11/2007 | Kasai et al. ................ 96/74 |
| 2010/0037776 A1 | * | 2/2010 | Chan ................ 96/80 |
| 2010/0089234 A1 | * | 4/2010 | Khoury ................ 95/81 |
| 2011/0096457 A1 | * | 4/2011 | Gefter et al. ................ 361/230 |

\* cited by examiner

DEVICE FOR COLLECTING PARTICLES THAT HAVE A STRONG ELECTRON AFFINITY

This application is the U.S. National Phase of, and Applicants claim priority from, International Application Number PCT/EP2009/065740 filed 24 Nov. 2009 and German Patent Application No. 102008059113.0 filed 26 Nov. 2008, which are incorporated herein by reference.

BACKGROUND

The invention relates to a device for collecting particles that have a strong electron affinity, particularly explosive particles from a gas.

The increasing use of explosives in terrorist attacks is a generally known security problem. Protecting civilian and military infrastructures from individuals and vehicles that transport improvised explosive devices currently represents a major challenge. Indications of concealed explosive material can be obtained with the aid of "BULK methods" (X-ray, terahertz, NMR detection). Another method for evidence collection methods is classed as "trace detection". In trace detection, gases that emanate from the concealed explosives are detected. In conjunction with sniffer dogs, this method relies primarily on ion mobility spectrometers (IMS) that can detect trace gases in a concentration range of $(10^{-9})$ ppb. In IMS detection of explosives, particular use is made of fact that the molecular structures of most explosives include nitro groups, which have a strong electron affinity. An important distinguishing criterion with respect to other substances that occur in trace amounts is therefore that explosives have a high tendency to form negative ions. These substances can then be differentiated further in IMS measurement via various runtimes in the IMS drift tube. One difficulty with detecting gas in this way is that many explosives, especially materials that are used extensively in military applications, have an exceptionally low vapour pressure, which severely hinders their detectability using gas detection methods.

SUMMARY

The object of the present invention is therefore to provide a device for collecting particles that have a strong electron affinity, particularly explosive particles from gas, which also enables collection of microscopically small particles having a diameter in the range from $0.1\mu$ to $10\mu$ in a much larger volume of analytically uninteresting particles from a suspicious object. Since the concentration of relevant particles is so low, the analytically irrelevant attendant particles may possibly create strong background signals in IMS detection, making it more difficult or entirely impossible to reliably detect these particles, particularly explosive particles.

This object is solved according to the invention by the features described in claim 1. Advantageous refinements of the inventive thought are presented in the subordinate claims and the description.

The device according to the invention enables particles having strong electron affinity to be separated out of the surrounding air and collected so that, in a subsequent step, particularly vaporisation, they may be converted into detectable gases. In this context, the flow of gas, particularly the flow of air, is guided together with the particles into an electrical field, wherein corona discharge takes place on at least one ionising electrode, providing electrons that ionise the molecules with high electron affinity in the surrounding air, particularly oxygen, thereby creating a plasma. Particles with stronger electron affinity than these ions then receive the excess electrons and thus become charged. Charging by corona discharge is thus effected indirectly. These particles, which are now negatively charged, will now be attracted to the positively charged collector electrode by the electrical field. The particles are collected there.

According to an advantageous refinement of the invention, the collector electrode is furnished with an electrically insulating layer for this purpose, on which the particles collect and after a given period are removed from the layer or vaporised directly on the layer by means of heaters.

Such an electrically insulating layer may be a separate substrate, made from oxidised silicon, for example.

In a second embodiment, the collector electrode is disposed in a transverse channel through which gas passes and in which the particles that accumulate on the collector electrode are neutralised and subsequently transported away by the gas that is passed through the transverse flow channel and fed to a downstream analysis device.

In a third embodiment of the invention, two longitudinal electrode meshes are disposed between two outer ionising electrodes, wherein the collector electrode is arranged between and downstream of these longitudinal electrode meshes. In this context, mutually synchronised voltage profiles at the four electrodes divert the negatively charged particles to the middle, that is to say the region between the longitudinal electrode meshes, from where they migrate to the collector electrode.

In a fourth embodiment of the invention, at least one negatively charged ionisation tip ring is present inside the flow channel and arranged concentrically therewith, and whose downstream edge is provided with ionisation tips, and with at least one negatively charged field ring further downstream, wherein a rod-shaped, passivated collector electrode is arranged also concentrically in the middle of the flow channel. In this embodiment, the negatively charged particles are moved radially inwardly after charging, and there they are either concentrated on the passivated collector electrode or guided into an extraction pipe.

In a fifth embodiment of the invention, the wall of the rotationally symmetrical flow channel is constructed as the collector electrode, and the rod-shaped ionising electrode is disposed centrically therein, wherein the flow channel wall has a radial outlet in at least one annular section, which outlet is furnished with a gas-permeable collecting layer that is largely impermeable for the particles. In a flushing step, the collected particles are then extracted from the collecting layer, which preferably has the form of a non-woven fabric, by a stream of flushing gas and then forwarded to analysis.

SUMMARY OF THE DRAWINGS

The invention will be explained in greater detail in the following with reference to the accompanying drawing. In the drawings.

DETAILED DESCRIPTION

Figure 1:
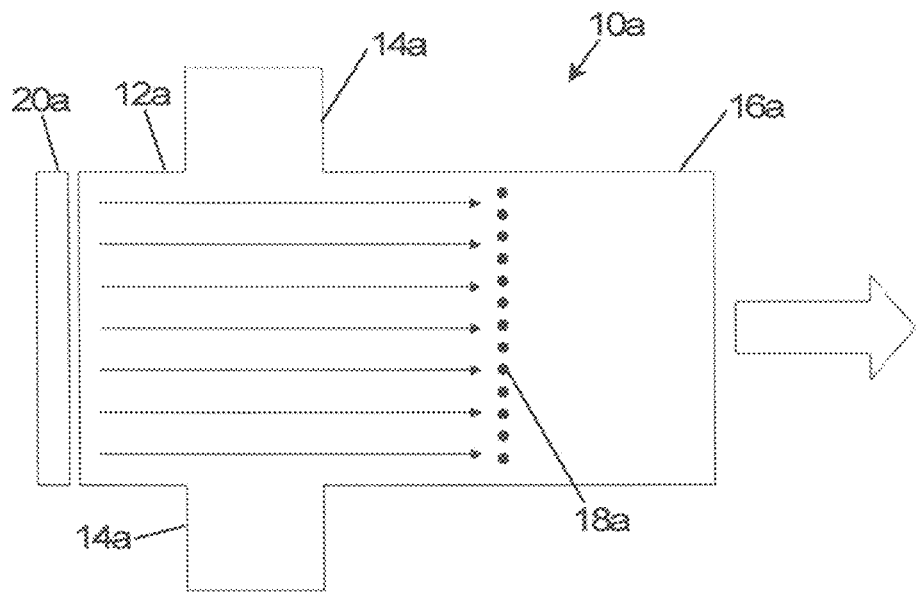
FIG. 1 is a diagrammatic representation of a first embodiment of the invention.
Figure 2:
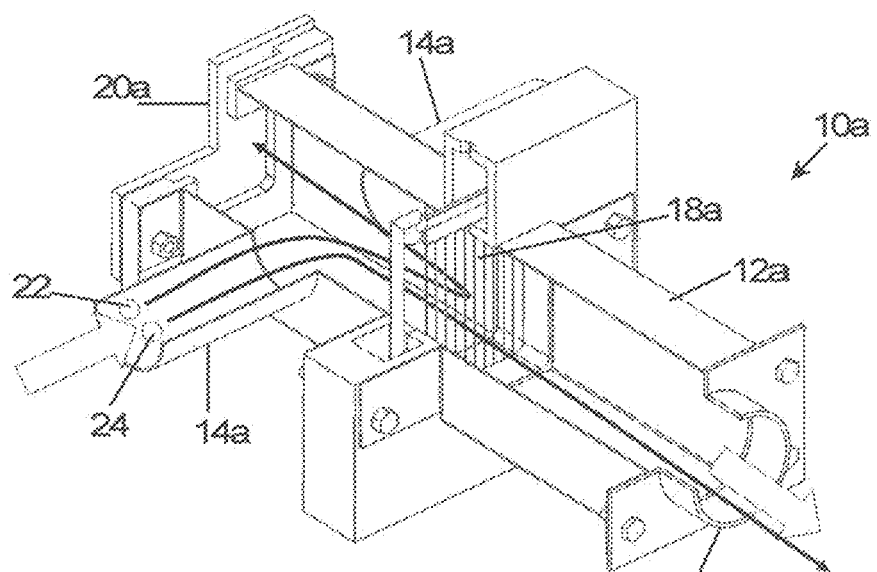
FIG. 2 is a perspective view of the embodiment of FIG. 1 with partial cutaway.

FIGS. 1 and 2 show a first preferred embodiment of a particle collecting device 10a, wherein the device is shown diagrammatically in FIG. 1 and in perspective with partial cutaway in FIG. 2. This particle collecting device 10a essentially consists of a flow channel 12a and two gas inflow channels 14a arranged opposite one another with respect to this flow channel 12a. A wire mesh is arranged across flow channel 12a between these inflow channels 14a and the downstream open end 16a of flow channel 12a, and serves as ionising electrode 18a. A collector electrode 20a is provided at the end of flow channel 12a opposite to outlet end 16a of flow channel 12a, and closes flow channel 12a off in this direction. Collector electrode 20a may be detachable or it may be provided with a scraper device that serves to remove particles deposited thereon. Alternatively, collector electrode 20a might also have a design such as is illustrated and explained in the following FIG. 3.

In operation, a stream of air with particles having strong affinity is sucked into inflow channels 14a via suction devices that are not shown and diverted through flow channel 12a (to the right in FIG. 1), flowing around wire mesh 18a and exiting at flow channel outlet 16a.

Initially, both particles are electrically neutral; one has strong electron affinity, the other has weak electron affinity.

A voltage potential in the range of 5000 Volt is applied between ionising electrode 18a and collector electrode 20a, wherein ionising electrode 18a is charged negatively and collector electrode 20a is charged positively. FIG. 2 shows a particle 22 with strong electron affinity and a neutral particle 24 side by side and their respective paths after entering particle collecting device 10a. This shows that after passing through gas inflow channel 14a neutral particle 24 enters flow channel 12a and passes through wire mesh 18a unaffected to exit flow channel 12a through flow channel outlet 16a. On the other hand, after entering flow channel 12a a particle with strong electron affinity 22 moves towards wire mesh 18a and undergoes indirect surface discharge due to the high field strength in the vicinity of the individual, negatively charged devices of wire mesh 18a, which causes a corona discharge, so that these particles become charged with electrons and are consequently accelerated towards collector electrode 20a by the electrical field between ionising electrode 18a and collector electrode 20a. The particles with strong electron affinity are deposited on the surface of collector electrode 20a. This collector electrode may then be removed and transferred to the thermal desorption system of an ion mobility spectrometer (IMS) where chemical composition may then be determined.

Figure 3:
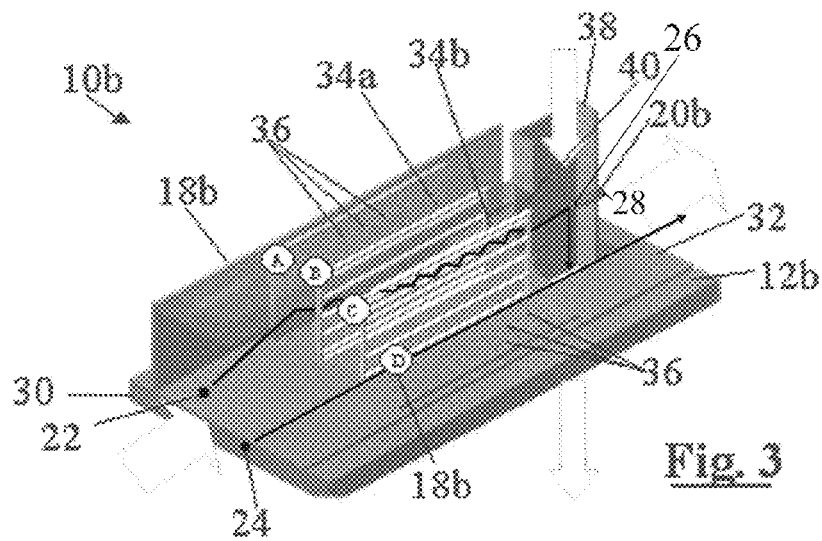
FIG. 3 is a perspective view of a second embodiment of the invention (wall not shown)
Figure 4:
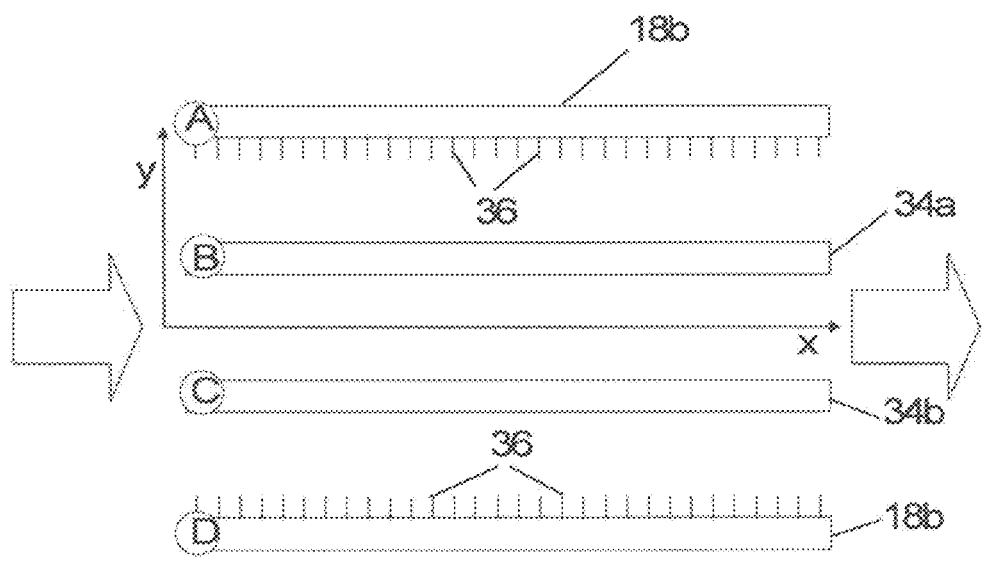
FIG. 4 is a diagrammatic representation of the electrode arrangement in the design of FIG. 3.

In this embodiment, collector electrode 20a is provided with an electrically insulating layer to prevent it from discharging to the positively charged electrode again and particles becoming concentrated there instead. FIGS. 3 and 4 show a second embodiment of the invention, FIG. 3 showing a perspective view without the flow channel and FIG. 4 showing a diagrammatic view of the four longitudinal mesh electrodes.

This embodiment of particle collecting device 10b has a flow channel 12b with rectangular cross-section, of which only the bottom and one side wall are shown in FIG. 3. The second side wall and top wall are absent. Flow channel 12b has an inlet 30 and an outlet 32, between which two longitudinal meshes 34a, 34b are arranged at a distance from one another. Two ionising electrodes 18b furnished with a plurality of ionising tips 36 that project into flow channel 12b are provided along the two side walls, and the increased field strength causes corona discharges to take place at the tips, indirectly create a charge in the particles with strong electron affinity. A transverse flow channel 38 with an aperture 40 is arranged between the two longitudinal electrode meshes 34a, 34b, and collector electrode 20b is disposed inside this. A gas (preferably air) flows through transverse flow channel 38 and carries the particles entering through aperture 40 with it, and may be directed to a collecting device.

Figure 5:
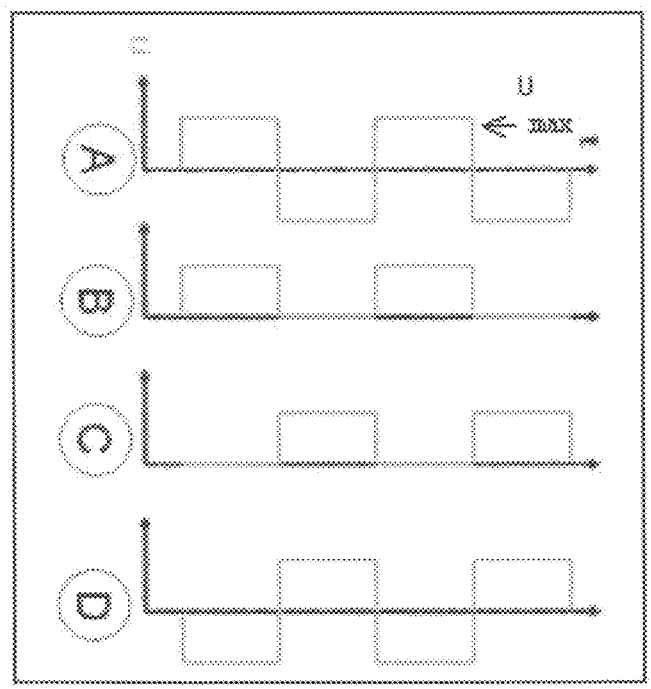
FIG. 5 is a representation of voltage profiles in the electrodes of FIG. 4.

Ionising electrodes 18b and longitudinal mesh electrodes 34a, 34b are connected to a generator, not shown, which generates a rectangular wave with high voltage amplitude, in the range of 4000 Volt. In the longitudinal mesh electrodes 34a, 34b, the voltage only oscillates in the positive range, while the oscillations along the two outer ionising electrodes 18b are generated in both positive and negative voltage ranges. At the same time, the oscillations of the left and right channel sides (that is to say of left ionising electrode 18b) and of the adjacent longitudinal electrode mesh 34a are offset by a phase angle of 90° with respect to the right ionising electrode 18b and the right longitudinal electrode mesh 34b as is shown in FIG. 5.

FIG. 3 shows the path of a particle 22 with strong electron affinity and that of a neutral particle 24, which migrates in a straight line through flow channel 12b without deviation (except for fluid mechanical flow movements caused by the presence of the meshes or transverse flow channel 38).

The particles with strong electron affinity are charged indirectly by corona discharge at ionising tips 36, and because they now carry a negative electrical charge they are accelerated in the electrical field between ionising electrodes 18b and longitudinal mesh electrodes 34. Because of the rectangular wave of the voltage, the direction of the electrostatic force changes with the voltage frequency. This arrangement causes the electrical field to be centred in the outer areas (that is to say between the ionising electrodes and the adjacent longitudinal mesh electrodes 34 in the same way as a monotonic function in mathematics. In the inner area, between the two longitudinal electrode meshes 34a, 34b, the force alternates by the same amount, theoretically resulting in a delta oscillation orbit, which remains effectively neutral. The effect of this arrangement is that all negatively charged particles are focussed in the central area and enter transverse flow channel 38 through aperture 40 at the end of the ionising section, where they come into contact with collector electrode 20b and are neutralised before being carried away into the transverse flow channel by the gas stream. A vaporisation device 28 (e.g., heating device or radiating device) can be provided, such as behind the collector device 20b, which vaporises the particles that have collected on the collector electrode 20b.

In this embodiment, the electrically insulating layer 26 on collector electrode 20b consists of a 4×4 $cm^2$ silicon wafer, which is removed and undergoes thermal desorption after a certain period.

Figure 6:
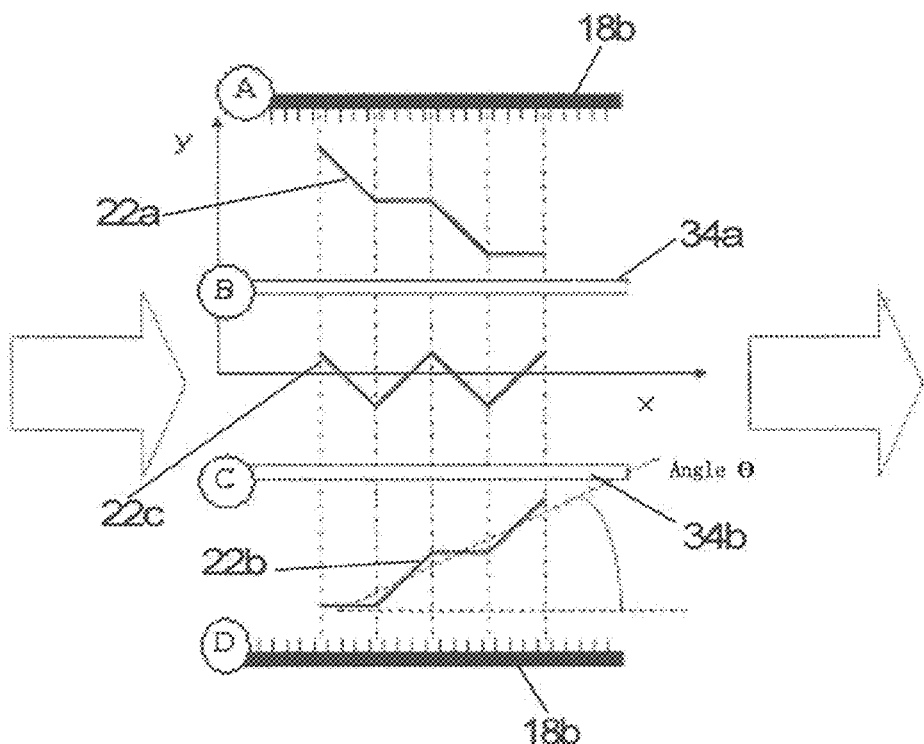
FIG. 6 is a representation of the particle migration between the electrode arrangement of FIG. 4 when voltage is applied as shown in FIG. 5.

FIG. 6 is a schematic diagram showing the path of movement of particles with strong electron affinity depending on their point of entry relative to meshes 18, 34 when passing through the meshes. A particle 22a with strong electron affinity that enters between ionising electrode 18b and the adjacent longitudinal electrode mesh 34a is moved inwards towards the longitudinal electrode mesh 34a by the voltage profile shown in FIG. 5 during phases in which a negative voltage is at ionising electrode 18b, and during the alternative phase, in which positive voltages are at both electrodes 18b, 34a it is carried along in the direction of movement of the air stream, essentially unaffected, so that over the course of many voltage cycles a general movement towards the middle results. On the other side, that is to say between ionising electrode 18b and the neighbouring longitudinal electrode mesh 34b, the same applies in mirror image for a particle 22b with strong electron affinity, resulting in a general movement of this particle 22b towards the middle. Consequently, an average movement is created in a direction at an angle θ to the direction of flow.

For a particle 22c with strong electron affinity that enters between the two longitudinal electrode meshes 34a, 34b, the alternating cycles of positive voltage at these meshes moves the particle in an essentially zigzag path corresponding to the rhythm of the voltage cycles, on average the path is thus parallel to the direction of flow.

Overall, therefore, particles 22 with strong electron affinity are moved towards the middle so that they may be collected in the transverse flow channel 38 shown in FIG. 3.

Figure 7:
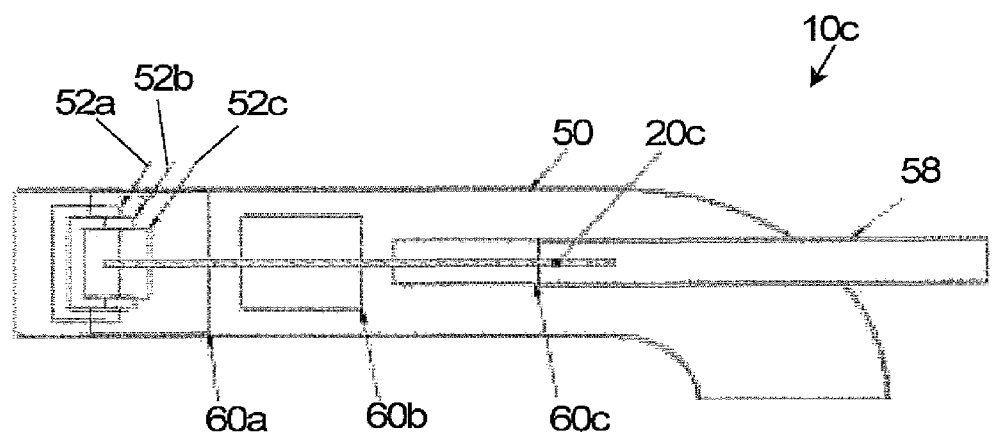
FIG. 7 is a diagrammatic cross-sectional representation of a third embodiment of the invention.

FIG. 7 is a diagrammatic cross-sectional view of a third embodiment of a particle collecting device 10c that essentially consists of a round jacket pipe 50 which includes three ionising tip rings 52a, 52b, 52c arranged concentrically and with axial offset from the outside inwards in the direction of flow in the area of the intake end. In the embodiment shown, the end of jacket pipe 50 closest to the flow outlet is curved. Ionising tip rings 52a, 52b, 52c have a jagged rear edge 54 with sharp points to form ionising tips, as shown diagrammatically in FIG. 8. Negative voltages are present in each of the ionising tip rings 52a, 52b, 52c and these diminish in strength progressively from the first ionising tip ring 52a to the third 52c.

A rod-shaped, passivated collector electrode 20c is provided coaxially with jacket tube 50 and opens into a collecting pipe 58 that is concentric with jacket tube 50. Three field rings 60a, 60b, 60c with progressively smaller diameters are also arranged axially one after the other and concentrically with jacket pipe 50, each having negative voltages that diminish progressively from the first field ring 60a to the third 60c.

Figure 8:
FIG. 8 is a detail from FIG. 7.

In operation, the air flow in FIG. 8 enters jacket pipe 50 at the left end. The conditions prevailing at ionising tip rings 52a, 52b, 52c indirectly cause the particles with strong electron affinity to become negatively charged and then to move towards the centre axis, that is to say the central collector electrode 20c due to the repellent force inside negatively charged field rings 60a, 60b, 60c. Thus the motion vectors engendered by the electrical fields acting on the particles with strong electron affinity are added to the motion vector created by the flow, and the particles move in a curved trajectory towards the collector electrode. Because the collector surface has been passivated, the particles are not able to lose their negative charge, so they remain stuck to the surface as a result of the passivation. Over time, a corresponding number of particles then collects there.

There are two preferred possibilities for removing the particles from the collector. In one embodiment, collector electrode 20c is negatively charged for a short time, so that the particles become slightly separated from the collector electrode and are carried away by the largely laminar flow in jacket pipe 50 and collecting tube 58. For this, the negative charge time at collector electrode 20c must be so short that the separation between the charged particles and collector electrode 20c is very small.

Alternatively collector electrode 20c may be constructed such that it may be detached axially and removed—to the right in the drawing—in which case a scraper device is then required to scrape the particles off of collector electrode 20c. In this design, collector tube 58 may be dispensed with.

Figure 9:
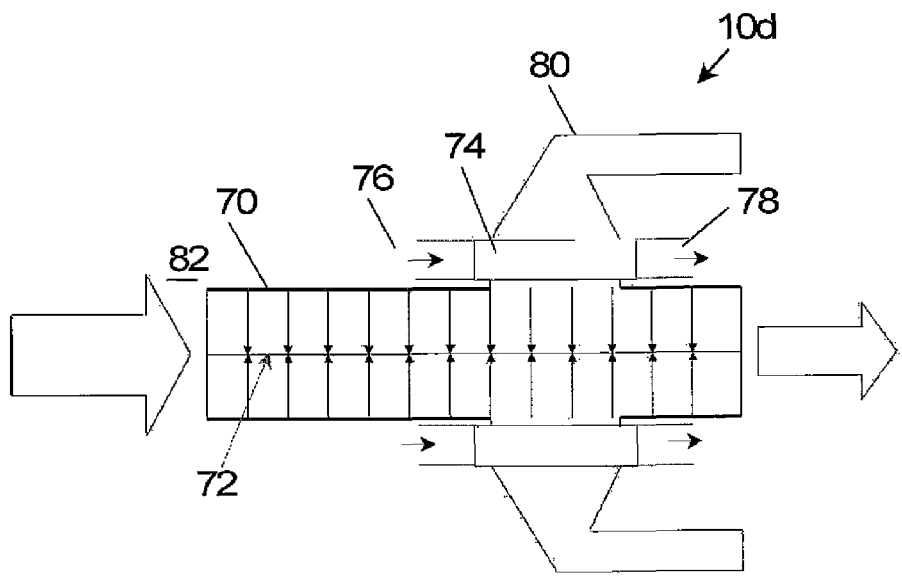
FIG. 9 is a schematic diagram of a fourth embodiment of the invention.
Figure 10:
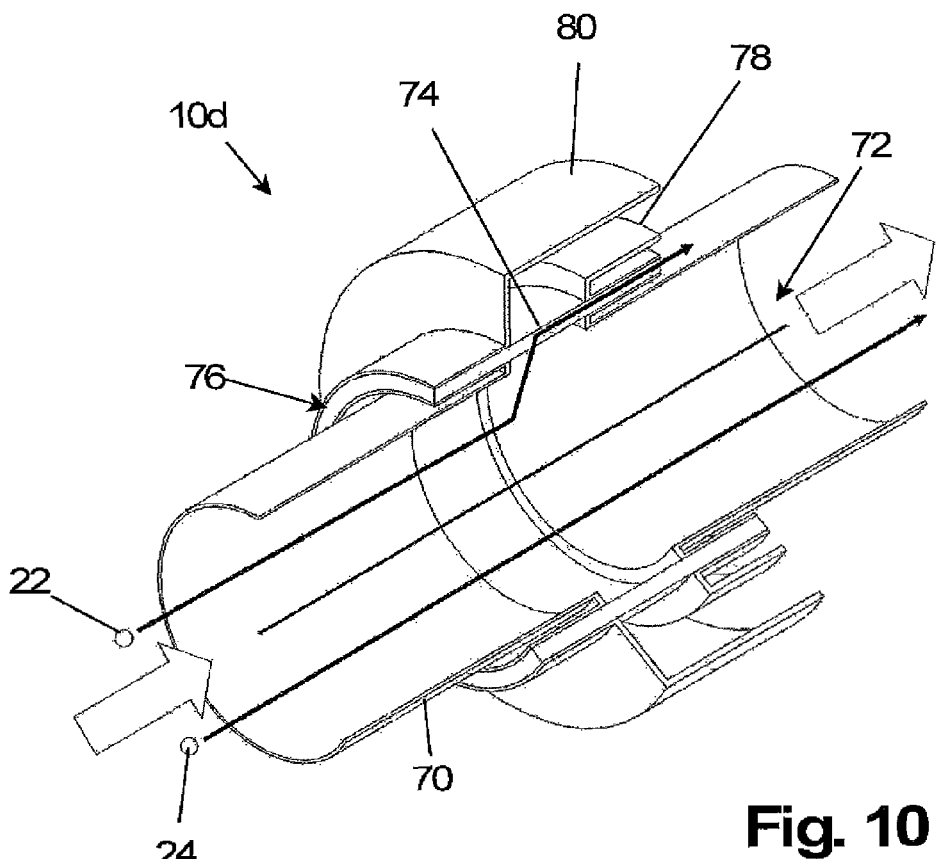
FIG. 10 is perspective view of the design of FIG. 9 with partial cutaway.

FIGS. 9 and 10 are respectively diagrammatic and perspective representations of a fourth preferred embodiment of a particle collecting device 10d, which consists essentially of a positively charged sheathed electrode 70 with a negatively charged corona electrode 72 arranged in the middle thereof. Sheathed electrode 70 has an annular outlet surrounded by a non-woven fabric filter 74 at a distance from the inlet end. This annular element 74 has a transverse flow inlet 76 and a transverse flow outlet 78, also a suction duct 80. FIG. 10 shows the paths of a particle 22 with strong electron affinity and that of a particle 24 with weak electron affinity. The particle-loaded stream enters sheathed electrode 70 at 82, whereupon the particles with strong electron affinity are charged indirectly at corona electrode 72 and then moved radially outwardly. Air is extracted from the main stream via suction duct 80, and the electrically charged particles that are concentrated close to the wall are carried with it, entering and becoming trapped in non-woven fabric filter 74. Non-woven fabric filter 74 has a pore size that decreases from the inside out, so that the larger particles are trapped deeper inside and the smaller particles are trapped towards the outside.

After a suitable period of time, a stream of gas is passed through non-woven fabric filter 74 from transverse flow inlet 76 to transverse flow outlet 78, perpendicularly to the previous flow direction, so that the particles with strong electron affinity that are trapped in the non-woven fabric filter 74 are removed therefrom through transverse flow outlet 78 and forwarded to a measuring device, which is not shown.

The invention claimed is:

1. A particle collecting device to collect particles with strong electron affinity the particle collecting device comprising:
    a flow channel having sidewalls;
    electrode plates disposed along the sidewalls, each of the electrode plates having a plurality of ionizing tips that protrude into the flow channel such that the particles with strong electron affinity are chargeable indirectly by a corona discharge at the ionizing tips;
    longitudinal electrode meshes disposed at a distance from one another in the flow channel; and
    an electrically positive collector electrode disposed between and downstream from the longitudinal electrode meshes such that the particles with the strong electron affinity are movable to the collector electrode to be collected.

2. The particle collecting device as recited in claim 1, wherein the particle collecting device comprises an electrically insulating layer disposed in front of the collector electrode, on which the particles with strong electron affinity accumulate.

3. The particle collecting device as recited in claim 2, wherein the electrically insulating layer is removable.

4. The particle collecting device as recited in claim 2, wherein the collector electrode is disposed in a transverse flow channel through which a gas flows, and the particles with strong electron affinity are neutralized on the collector electrode and carried away by the gas.

5. The particle collecting device as recited in claim 1, wherein the particle collecting device comprises a vaporization device that vaporizes the particles with strong electron affinity that have collected on the collector electrode.

6. The particle collecting device as recited in claim 1, wherein rectangular voltages in a same phase are applied to each longitudinal electrode mesh and adjacent electrode plate pair of two electrode pairs, wherein a voltage profile at a respective longitudinal electrode mesh only matches a voltage profile at the adjacent electrode plate in a positive range of the same phase, and voltage profiles of the two electrode pairs are offset by 90° relative to one another.

7. The particle collecting device as recited in claim 1, wherein the particle collecting device comprises a radiating device arranged behind the collector electrode to heat the collector electrode and convert the particles with strong electron affinity collected on the collector electrode to vapor form.

8. The particle collecting device as recited in claim 1, wherein the particle collecting device comprises a collector chamber in which the collector electrode is disposed, the collector chamber being open towards a stream of the particles with strong electron affinity such that the stream cannot flow around the collector chamber.

\* \* \* \* \*